(12) United States Patent
Feldman et al.

(10) Patent No.: US 8,579,829 B2
(45) Date of Patent: Nov. 12, 2013

(54) SYSTEM AND METHOD FOR MONITORING BREATHING

(75) Inventors: Doron Feldman, Williamsville, NY (US); Jerrold Lerman, Buffalo, NY (US); Ronen Feldman, Ellicott City, MD (US); John Moser, Severna Park, MD (US); Uri Feldman, Columbia, MD (US)

(73) Assignee: Linshom L.P., Williamsville, NY (US)

( * ) Notice: Subject to any disclaimer, the term of this patent is extended or adjusted under 35 U.S.C. 154(b) by 753 days.

(21) Appl. No.: 12/759,788

(22) Filed: Apr. 14, 2010

(65) Prior Publication Data

US 2010/0268105 A1 Oct. 21, 2010

Related U.S. Application Data

(60) Provisional application No. 61/170,594, filed on Apr. 17, 2009.

(51) Int. Cl.
*A61B 5/08* (2006.01)

(52) U.S. Cl.
USPC .......................................... 600/537; 600/529

(58) Field of Classification Search
USPC ................................................ 600/529–543
See application file for complete search history.

(56) References Cited

U.S. PATENT DOCUMENTS

| | | |
|---|---|---|
| 3,232,288 A | 2/1966 | Krobath |
| 3,513,832 A | 5/1970 | Klemm et al. |
| 3,903,876 A | 9/1975 | Harris |
| 3,999,537 A | 12/1976 | Noiles |
| 4,420,001 A | 12/1983 | Hearne |
| 4,646,750 A | 3/1987 | Williams |
| 5,069,222 A | 12/1991 | McDonald, Jr. |
| 5,161,541 A | 11/1992 | Bowman et al. |
| 5,190,048 A | 3/1993 | Wilkinson |
| 5,193,347 A | 3/1993 | Apisdorf |
| 5,197,294 A | 3/1993 | Galvan et al. |
| 5,311,875 A | 5/1994 | Stasz |
| 5,355,893 A * | 10/1994 | Mick et al. ................... 600/532 |
| 5,357,975 A | 10/1994 | Kraemer et al. |
| 5,385,020 A | 1/1995 | Gwilliam et al. |

(Continued)

OTHER PUBLICATIONS

Sleep Review The Journal for Sleep Specialists; http://www.sleepreviewmag.com/issues/articles/2008-12_03d.asp; 5 pages.

(Continued)

*Primary Examiner* — Navin Natnithithadha
*Assistant Examiner* — Eric Messersmith
(74) *Attorney, Agent, or Firm* — Rosenberg, Klein & Lee

(57) ABSTRACT

A system for monitoring the breathing status of a patient comprises a first temperature sensor and a second temperature sensor. The first temperature sensor is arranged to measure the temperature of the breathing gas of a patient. The second temperature sensor is arranged to measure an ambient temperature of the patient's surroundings. A controller is included, wherein the controller is programmed to determine a plurality of breathing-gas temperatures over time by way of a first signal received from the first temperature sensor and at least one ambient temperature using a second signal received from the second temperature sensor. The controller is programmed to analyze the plurality of breathing-gas temperatures and the at least one ambient temperature to determine a breathing status of the patient. The present invention may be embodied as a method for monitoring the breathing status of a patient.

15 Claims, 2 Drawing Sheets

(56) References Cited

U.S. PATENT DOCUMENTS

| | | | |
|---|---|---|---|
| 5,832,592 A | 11/1998 | Bowman et al. | |
| RE36,242 E | 6/1999 | Apisdorf | |
| 5,964,712 A | 10/1999 | Kubo et al. | |
| 6,085,576 A | 7/2000 | Sunshine et al. | |
| 6,155,986 A | 12/2000 | Brydon et al. | |
| 6,158,434 A | 12/2000 | Lugtigheid et al. | |
| 6,165,133 A | 12/2000 | Rapoport et al. | |
| 6,234,006 B1 | 5/2001 | Sunshine et al. | |
| 6,272,933 B1 | 8/2001 | Gradon et al. | |
| 6,368,287 B1 * | 4/2002 | Hadas | 600/529 |
| 6,418,783 B2 | 7/2002 | Sunshine et al. | |
| 6,523,538 B1 | 2/2003 | Wikefeldt | |
| 6,555,821 B1 | 4/2003 | Himberg et al. | |
| 6,658,915 B2 | 12/2003 | Sunshine et al. | |
| 6,669,649 B2 | 12/2003 | Kahn | |
| 6,837,095 B2 | 1/2005 | Sunshine et al. | |
| 6,840,955 B2 | 1/2005 | Ein | |
| 6,883,364 B2 | 4/2005 | Sunshine et al. | |
| 6,954,944 B2 | 10/2005 | Feher | |
| 7,028,687 B1 | 4/2006 | Silver et al. | |
| 7,089,780 B2 | 8/2006 | Sunshine et al. | |
| 7,101,341 B2 | 9/2006 | Tsukashima et al. | |
| 7,297,120 B2 | 11/2007 | Tsukashima et al. | |
| 7,354,195 B2 | 4/2008 | Sakano | |
| 7,415,126 B2 | 8/2008 | Breed et al. | |
| 7,418,981 B2 | 9/2008 | Baker et al. | |
| 7,438,072 B2 | 10/2008 | Izuchukwu | |
| 7,483,805 B2 | 1/2009 | Sparks et al. | |
| 7,525,663 B2 | 4/2009 | Kwok et al. | |
| 2001/0037071 A1 | 11/2001 | Lingo, Jr. et al. | |
| 2001/0039824 A1 | 11/2001 | Sunshine et al. | |
| 2002/0124631 A1 | 9/2002 | Sunshine et al. | |
| 2002/0178789 A1 | 12/2002 | Sunshine et al. | |
| 2003/0199804 A1 | 10/2003 | Ahlmen et al. | |
| 2004/0069046 A1 | 4/2004 | Sunshine et al. | |
| 2004/0082872 A1 | 4/2004 | Von Bahr et al. | |
| 2004/0186389 A1 | 9/2004 | Mault et al. | |
| 2004/0210151 A1 | 10/2004 | Tsukashima et al. | |
| 2004/0210153 A1 | 10/2004 | Tsukashima et al. | |
| 2005/0061056 A1 | 3/2005 | Sunshine et al. | |
| 2005/0131504 A1 | 6/2005 | Kim | |
| 2006/0037613 A1 | 2/2006 | Kwok et al. | |
| 2006/0196505 A1 | 9/2006 | Izuchukwu | |
| 2007/0068811 A1 | 3/2007 | Tsukashima et al. | |
| 2007/0088334 A1 | 4/2007 | Hillis et al. | |
| 2007/0167855 A1 * | 7/2007 | Shin et al. | 600/533 |
| 2008/0061238 A1 | 3/2008 | Hok et al. | |
| 2008/0078382 A1 | 4/2008 | LeMahieu et al. | |
| 2008/0082018 A1 | 4/2008 | Sackner et al. | |
| 2008/0183094 A1 | 7/2008 | Schonfuss et al. | |
| 2008/0243056 A1 | 10/2008 | Hillis et al. | |
| 2008/0281220 A1 | 11/2008 | Sharifpour | |
| 2009/0038615 A1 | 2/2009 | Bradley | |
| 2009/0078120 A1 | 3/2009 | Kummer et al. | |
| 2009/0241947 A1 * | 10/2009 | Bedini et al. | 128/203.14 |
| 2010/0007889 A1 | 1/2010 | Van Kesteren | |
| 2010/0090650 A1 | 4/2010 | Yazami et al. | |
| 2010/0175556 A1 | 7/2010 | Kummer et al. | |

OTHER PUBLICATIONS

Shochat et al.; The SleepStrip™: an apnoea screener for the early detection of sleep apnoea syndrome; http://erj.ersjournals.com/content/19/1/121.full; 7 pages.

Anesthesia Breath Detection Products; http://salterlabs.com; 1 page.

ThermiSense®; Oral/Nasal Thermal Airflow Sensing System; http://salterlabs.com/index.cfm?fuseaction=products.product&product_id=15&category_i . . . ; 3 pages.

Salter-Style® 1600F High Flow Cannula; http://salterlabs.com/index.cfm?fuseaction=products.product&product_id=27&category_i . . . ; 3 pages.

Salter-Style® TLCannula™; http://salterlabs.com/index.cfm?fuseaction=products.product&product_id=26&category_i . . . ; 3 pages.

* cited by examiner

SYSTEM AND METHOD FOR MONITORING BREATHING

CROSS-REFERENCE TO RELATED APPLICATION

This application claims the benefit of priority to U.S. provisional patent application Ser. No. 61/170,594, filed on Apr. 17, 2009, the disclosure of which is incorporated herein by reference.

FIELD OF THE INVENTION

The invention relates to devices and methods of monitoring breathing.

BACKGROUND OF THE INVENTION

Brain damage and death are direct consequences of prolonged apnea, particularly when combined with hypoxia. The problem of hypoxia and apnea are particularly troublesome when a patient is sedated, as is the case in many medical procedures. Diagnosing hypoventilation and apnea by detecting reduced breathing frequency or breath volume (known as tidal volume) may prompt an early intervention to stimulate breathing, relieve airway obstruction, and restore effective respiration. It is safer to detect inadequate or absent respiration early and restore respiration to normal before hypoxia occurs, than to have a patient suffer from hypoxic-ischemic brain damage.

Two important components of gas exchange in the lungs are oxygenation and ventilation. Oxygenation is commonly monitored non-invasively using pulse oximetry. In contrast, ventilation can only be monitored continuously and non-invasively by measuring the carbon dioxide partial pressure in the exhaled breath. However, there are no inexpensive carbon dioxide detectors that are portable (i.e., can be lifted by a human with a single hand without the aid of a machine).

Ventilation may be measured by examining movement of the chest and ribcage using sophisticated monitors, such as those used in sleep studies. However, these monitors are expensive, cumbersome, non-transportable, and therefore are limited to use in a laboratory.

Currently, there are no devices that provide a non-invasive, portable and semi-quantifiable measure of ventilation in individuals whose airways are not instrumented. Such a device would be useful to detect breathing and measure respiratory rate, and would be particularly useful to detect inadequate respiration or apnea during and after sedation, and general and regional anesthesia, and in those in whom unexpected breathing obstruction (i.e., obstructive sleep apnea, Ondine's curse) or sudden respiratory arrest (i.e., after cleft palate surgery) may occur.

BRIEF SUMMARY OF THE INVENTION

The temperature of the exhaled breath may be a useful surrogate marker that tracks ventilation. The difference between the temperature of the exhaled breath and the ambient temperature is a useful metric that may be used to estimate the respiratory rate and the tidal volume. The invention can be embodied as a non-invasive, portable device that detects exhalation in living beings by continuously measuring and analyzing the temperature of the expired breath while using the room temperature (i.e., ambient temperature) as a reference. It is assumed that the ambient temperature differs from that of the exhaled gas. A device according to the invention may include a monitor to display a visual indication that the patient (human or animal) is breathing and that gas is being exhaled from the lungs. The invention can also measure the frequency of respiration and the approximate volume of a breath. An embodiment of the invention can detect effective respiration in a living being when they are at risk for airway obstruction, such as during, or after sedation with anesthetic medications and sedatives, during cardiac resuscitation, and in subjects who may cease to breathe effectively when asleep.

A system for monitoring the breathing status of a patient according to an embodiment of the present invention comprises a first temperature sensor and a second temperature sensor. The first temperature sensor may be arranged to measure the temperature of the breathing gas of a patient. The second temperature sensor may be arranged to measure an ambient temperature of the patient's surroundings. A controller may be included, wherein the controller is programmed to determine a plurality of breathing-gas temperatures over time by way of a first signal received from the first temperature sensor and at least one ambient temperature using a second signal received from the second temperature sensor. The controller may be programmed to analyze the plurality of breathing-gas temperatures and the at least one ambient temperature to determine a breathing status of the patient.

A maximum and/or minimum breathing-gas temperature during a time interval, such as a single respiratory cycle, may be determined from the plurality of breathing-gas temperatures. In the case where the controller determines both a maximum and a minimum breathing-gas temperature, the controller may calculate the mathematical difference between the maximum and minimum breathing-gas temperatures. A threshold $\Delta T_m$, representing a $\Delta T_m$ below which a problem may exist, may be compared with the calculated $\Delta T_m$ to determine the breathing-status of the patient. The controller may activate an alarm when the breathing status of the patient is determined to be unsatisfactory, for example, when the calculated $\Delta T_m$ is less than the threshold $\Delta T_m$.

A bias temperature may be calculated by subtracting the ambient temperature from an average breathing-gas temperature. The controller may selecte a threshold $\Delta T_m$ based on this calculated bias temperature.

The controller may have a memory device, which may have a look-up table with pre-determined threshold $\Delta T_m$ values. As such, the ambient temperature value, the bias temperature value, or both values may be used as input criteria to identify from the table a threshold $\Delta T_m$ appropriate to the input criteria used. The look-up table of the memory device may be a multi-dimensional look-up table, which contains pre-defined program steps that are based on different combinations of input criteria. The controller may determine a program step based on the ambient temperature, bias temperature, and/or $\Delta T_m$, and may execute the determined program step.

The controller may comprise a field-programmable gate array having a logic circuit, which may be programmed to use ambient temperature and bias temperature in order to determine the appropriate threshold $\Delta T_m$. Such a controller may be programmed to use a decision-tree to determine the appropriate threshold $\Delta T_m$ based on values of ambient temperature and bias temperature.

The present invention may be embodied as a method for monitoring the breathing of a patient wherein a first temperature sensor is used to measure the patient's breathing-gas temperature and a second temperature sensor is used to measure an ambient temperature. A controller is provided and programmed to determine a plurality of breathing-gas temperatures over time and at least one ambient temperature. The controller is programmed to analyze the plurality of breathing-gas temperatures and the at least one ambient temperature to determine a breathing status of the patient.

The controller may be programmed to determine a maximum breathing-gas temperature, a minimum breathing-gas temperature during a time interval, and/or a mathematical difference, $\Delta T_m$, between the maximum and minimum temperatures. The controller may be programmed to compare the calculated mathematical difference between the maximum and minimum breathing-gas temperatures with a threshold $\Delta T_m$. If the calculated $\Delta T_m$ is less than the threshold $\Delta T_m$, the breathing status of the patient is unsatisfactory. The controller may indicate the breathing status of the patient. For example, the controller may activate an alarm if the breathing status of the patient is unsatisfactory.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE INVENTION

Figure 1:
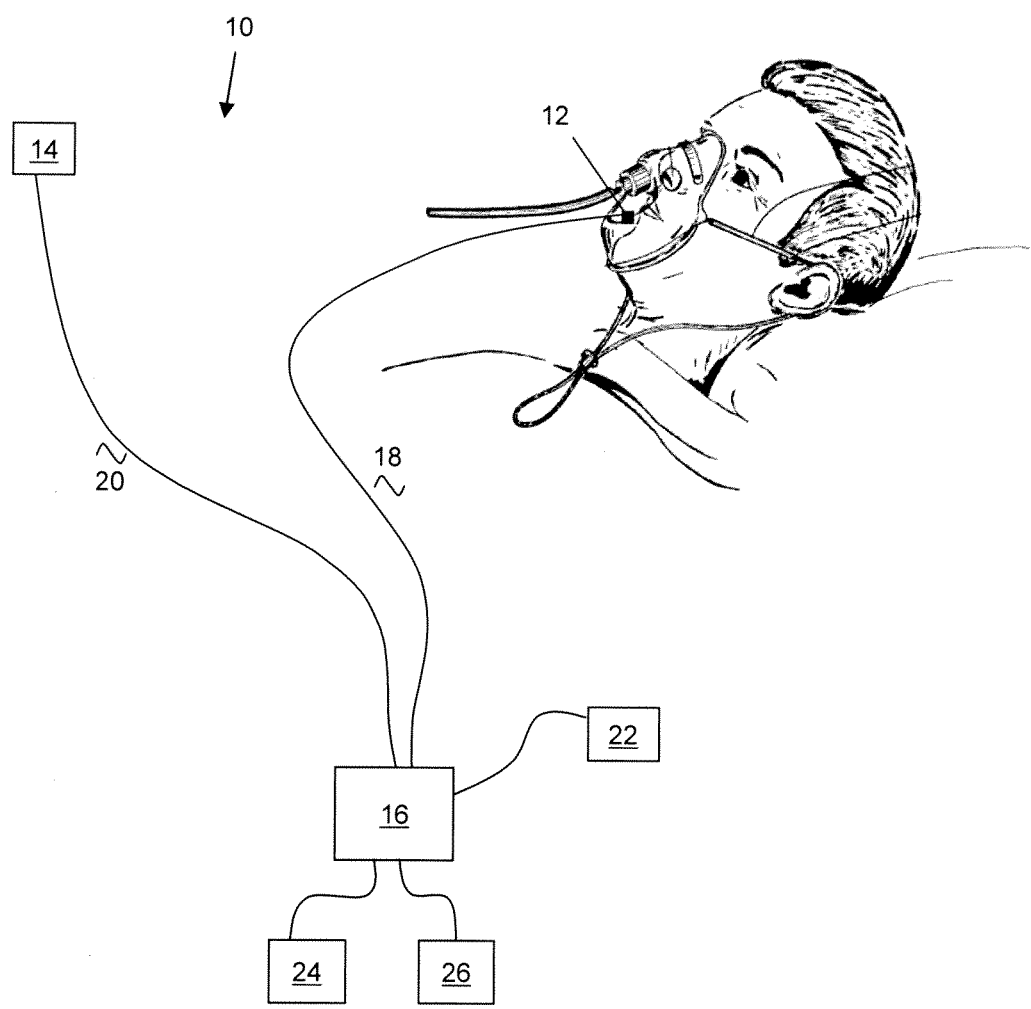
FIG. 1 is a schematic of a device according to an embodiment of the invention.

FIG. 1 depicts a system 10 for monitoring the breathing status of a patient according to an embodiment of the present invention. The system 10 comprises a first temperature sensor 12 and a second temperature sensor 14. The first and second temperature sensors 12, 14 may be, for example, thermistors. The first temperature sensor 12 may be arranged to measure the temperature of the breathing gas ("$T_m$") of a patient. The first temperature sensor 12 may be located within or adjacent to an oxygen delivery device, such as in the patient's breathing mask or adjacent to nasal prongs. In those patients in whom a tracheal tube is placed, the first temperature sensor 12 may be placed in the tube to verify the presence of breathing and to confirm the tube is within the trachea. This would be useful when capnography is not present (e.g., outside the hospital or in intensive care units) and when it is as a secondary monitor.

The second temperature sensor 14 may be arranged to measure an ambient temperature ("$T_a$") of the patient's surroundings. For example, the second temperature sensor 14 may be arranged to measure the air temperature of a room in which the patient is located.

The system 10 further comprises a controller 16 which may be programmed to determine a plurality of breathing-gas temperatures by way of a first signal 18 received from the first temperature sensor 12. For example, in the case where the first temperature sensor 12 is a thermistor, the first signal may be a change in voltage or current across the thermistor due to a temperature-induced change in resistance of the thermistor. The plurality of breathing-gas temperatures may be determined over a period of time, $T_m(t)$, such that the temperature at discreet points in time may be used to determine, for example, a maximum breathing-gas temperature during a time interval. The controller 16 may be programmed to determine at least one ambient temperature using a second signal 20 received from the second temperature sensor 14 during the time interval. The controller 16 may be programmed to analyze the plurality of breathing-gas temperatures and the at least one ambient temperature to determine a breathing status of the patient.

In an embodiment of a system 10 according to the present invention, the controller may be programmed to determine a maximum breathing-gas temperature, $Max(T_m(t))$, and/or a minimum breathing-gas temperature, $Min(T_m(t))$, during a time interval. The time interval may be, for example, the time for a single inhalation/exhalation cycle of the patient (a cycle of inhalation/exhalation is herein referred to as "a breathing period"). The temperature measured by the first temperature sensor 12 may be relatively low during patient inhalation (for example, when the air supplied to the patient is lower than the patient's body temperature). Accordingly, the temperature measured by the first temperature sensor 12 may be relatively high during patient exhalation because the breathing-gas has been warmed by the patient's body. In this way, the breathing period may be automatically determined by the controller by analyzing the plurality of breathing-gas temperatures to identify recurring local maximum temperatures, local minimum temperatures, or both.

In the case where the controller determines a maximum and a minimum breathing-gas temperature during a breathing period, the controller may calculate the mathematical difference, $\Delta T_m$, between the maximum and minimum breathing-gas temperatures. As such, for a given breathing period, $\Delta T_m$ may be calculated by the equation:

$$\Delta T_m = Max(T_m(t)) - Min(T_m(t)).$$

A threshold $\Delta T_m$ may be pre-determined, the threshold $\Delta T_m$ representing a $\Delta T_m$ below which a problem may exist. For example, if the actual $\Delta T_m$ of the patient is below a threshold $\Delta T_m$, the breathing mask may not be properly positioned on the patient, the patient may be improperly ventilated, and/or other issues may be present. The threshold $\Delta T_m$ may differ due to certain variables, such as, but not limited to, patient weight, ambient temperature, and core body temperature of the patient. Values of threshold $\Delta T_m$, taking these (or other) variables into account, may be pre-determined by, for example, clinical trials.

In an embodiment of a system 10 according to the present invention, the controller may be programmed to compare the calculated $\Delta T_m$ to a threshold $\Delta T_m$. In this way, the breathing status of the patient may be determined to be unsatisfactory if the calculated $\Delta T_m$ is below the threshold $\Delta T_m$. The controller may activate an alarm, for example, but not-limited to, an electronic bell 22 may chime, when the breathing status of the patient is unsatisfactory.

The threshold $\Delta T_m$ may be selected from a plurality of threshold $\Delta T_m$ values based on environmental factors. For example, the threshold $\Delta T_m$ may be selected based on the ambient temperature, $T_a$. As such, for example, if the patient's room is warm, the selected threshold $\Delta T_m$ may be lower than if the patient's room is cold.

A bias temperature, $T_{bias}$, may be calculated by subtracting the ambient temperature (alternatively, an average ambient temperature) from an average breathing-gas temperature, as in:

$$T_{bias} = Average(T_m(t)) - Average(T_a(t)).$$

In this way, $T_{bias}$ may be influenced by the temperature of gas provided to the patient and the temperature of the gas returned from the patient. The controller 16 may select a threshold $\Delta T_m$ based on this calculated $T_{bias}$.

The controller 16 may comprise a memory device 24, such as, but not limited to, a non-volatile memory chip. The memory device 24 may have a look-up table with pre-determined threshold $\Delta T_m$ values. As such, the ambient temperature value, the bias temperature value, or both values may be used as input criteria to identify from the table a threshold $\Delta T_m$ appropriate to the input criteria used. The resulting threshold $\Delta T_m$ may then be used in the comparison to calculate $\Delta T_m$ in order to determine the patient's breathing status. In this way, $T_a$ and/or $T_{bias}$ may be taken into account when determining whether the patient's breathing status is unsatisfactory.

The look-up table of the memory device 24 may be a multi-dimensional look-up table which contains pre-defined program steps that may be based on different combinations of input criteria, such as, but not limited to, $\Delta T_m$, $T_{bias}$, and $T_a$. For example, specific ranges of $\Delta T_m$, $T_{bias}$, and $T_a$ may identify in the look up table a next program step (e.g., sound an audible alarm) to be executed by the controller 16.

In a system 10 according to an embodiment of the present invention, the controller may be programmed to use a decision-tree to determine the appropriate threshold $\Delta T_m$ based on the values of $T_a$ and $T_{bias}$. For example, the controller may use the values of $T_a$ and $T_{bias}$ to identify a path in the decision-tree leading to a threshold $\Delta T_m$.

In a system 10 according to an embodiment of the present invention, the controller comprises a field-programmable gate array ("FPGA") 26 having a logic circuit. The FPGA 26 may be programmed to use $T_a$ and $T_{bias}$ to determine the appropriate threshold $\Delta T_m$. For example, the logic circuit may represent a decision-tree where values of $T_a$ and $T_{bias}$ may be used to identify a path in the decision-tree leading to a threshold $\Delta T_m$.

FIG. 1 depicts a device that is in keeping with the invention. The invention may include a pair of (non-self-heating) thermistors. The first thermistor (T1) indicates the temperature of the exhaled breath within a breathing apparatus, such as a face mask ($T_m(t)$). The location of thermistor (T1) within or near the breathing apparatus may be optimized to detect the maximum variation in the $T_m(t)$ signal during a breathing cycle. The optimal location will likely be in close proximity to the nares or mouth, and may be influenced by the shape of the breathing apparatus (mask or nasal prongs), and/or the location of the incoming oxygen flow within the mask. The second thermistor (T2) may indicate the ambient temperature ($T_a(t)$), that is, the temperature of the environment remote (within a few feet) from the breathing apparatus so as to be unaffected by the temperature of the exhaled breath. Both thermistors, T1 and T2, provide an analog voltage signal indicating the sensed temperature, and those analog voltage signals may be processed through an analog-to-digital converter ("ADC"). The ADC provides a digital indication of each temperature, $T_m(t)$ and $T_a(t)$, which may be made available to a digital microprocessor or to a field programmable gate array (FPGA) based device. The microprocessor or the FPGA based device may be programmed to ascertain the patient's breathing patterns based on the digital temperature measurements.

Also, the microprocessor may be programmed in other ways. For example, the microprocessor may be programmed to adjust its calculations of certain derived values. To illustrate, consider that $T_a(t)$ may be expected to change slowly with time and independently of the breathing status of the patient. Therefore, in order to provide a stable response while $T_a(t)$ is slowly changing, the microprocessor may be programmed to compensate for changes in $T_a(t)$ by using a look up table (that includes variables, such as estimated tidal volumes for age, weight and height, that may affect normal values for respiration) stored in its memory. The look up table may be generated from data obtained from clinical studies performed under a variety of ambient temperature conditions.

Effective breathing by the patient may be determined by comparing the magnitude of the values of the temperature variations during the breathing cycle in the vicinity of the patient's mouth and/or nose. Changes in the ambient temperature may be compensated with values pre-stored in a reference table. When using a microprocessor, the reference table values may be stored in a memory. When using an FPGA-based device, the reference table values may be programmed into the silicon. Portions of the reference table may be specific for the type of mask used (e.g., facemask or nasal prongs), the age or size category (infant, child or adult) of the patient, or other information in order to properly assess the breathing status of the patient.

The microprocessor may be programmed to obtain information provided by thermistors T1 and T2, and the ADC. Data derived from the temperature information may be used to determine the respiration status for the specific patient currently being monitored. For example, the microprocessor may be programmed to calculate (and thereby derive) a breathing rate and a size of the tidal volume using the temperature information. These values may then be used to provide a human interpretable indication of the patient's breathing status. For example, the indication of breathing status may be to illuminate an array of light emitting diodes to an extent needed to indicate to medical personnel that breathing is occurring, and possibly the extent to which breathing is occurring. Another indication of breathing status may be to activate an audio device in order to provide an alarm that can be heard by medical personnel when the patient's breathing is determined by the microprocessor to be inadequate or distressed. Information provided by the thermistors and collected by the microprocessor can also be packetized and transmitted to a remote data acquisition computer. The remote computer may provide enhanced processing, analysis and display capabilities. Long term trend graphs and visual verification of breathing patterns may be provided that can be used to assist in long duration studies and real time monitoring.

Information may be used to compensate for changes in the ambient temperature that are unrelated or of limited value to assessing a patient's breathing status. Two such pieces of information, $T_{bias}$ and $\Delta T_m$ may be derived as follows:

$$\text{Average } (T_m(t)) = \frac{1}{n}\sum_{t_1}^{t_n} T_m(t)$$

$$\text{Average } (T_a(t)) = \frac{1}{n}\sum_{t_1}^{t_n} T_a(t)$$

$$T(\text{bias}) = \text{Average } (T_m(t)) - \text{Average } (T_a)$$

The thermistor values may be tabulated every predetermined time $\Delta t$ that is much shorter than an expected breathing cycle. A typical value of $\Delta t$ would be 0.1 sec.

If needed, the "noise" in the stream of readings can be reduced by a simple algorithm. Such can be the so-called box-car algorithm, where the value of each reading is averaged with n previous and n subsequent readings, where n is a small number.

The maximum value $\text{Max}(T_m(t))$ and the minimum value $\text{Min}(T_m(t))$ within a breathing cycle may be derived by an algorithm that searches for maximum and minimum values respectively within an array of $T_m$ consecutive readings where m can be on the order of 10. Having $\text{Max}(T_m(t))$ and $\text{Min}(T_m(t))$, $\Delta T_m(t)$ may be determined by use of the following equation:

$$\Delta T_m(t) = \text{Max}(T_m(t)) - \text{Min}(T_m(t))$$

The magnitude of $\Delta T_m(t)$ and the corresponding $T_a(t)$ readings may be used to estimate the tidal volume (size of breath). The frequency of $Max(T_m(t))$ or $Min(T_m(t))$ values per minute may be used to derive the breathing rate.

Instead of a lookup table, FPGA based devices may be programmed to operate in several modes. The modes may be designed to indicate levels of breathing that are considered satisfactory for particular groups of patients. If the operator (physician, nurse or technician) deems the patient's breathing patterns to be satisfactory, he/she may select the desired operating mode and instruct the device to use those data as the base line. On the other hand, if the operator (physician, nurse or technician) deems the patient's breathing patterns to be unsatisfactory, he/she may select the desired operating mode based on stored data for the patient's age and weight and the breathing apparatus. (The selection of a desired operating mode may be done by a push button.) A deviation from the baseline by a pre-determined amount would sound an alarm.

The mathematical algorithms for $T_{bias}$ and $\Delta T_m$ may be used in a program that can control the microprocessor to produce $T_{bias}$ and $\Delta T_m$ values periodically. In conjunction with the reference table, the current values for $T_m$, $T_{bias}$, and $\Delta T_m$ may be used to complete or identify a set of instructions that will cause the microprocessor to produce an output, which indicates the breathing status of the patient.

In an embodiment of the invention, the reference table may be structured so that the current derived values for $T_a$ and $T_{bias}$ identify a threshold value for $\Delta T_m$ from the reference table. In such a device, the microprocessor may be programmed to compare the threshold value for $\Delta T_m$ obtained from the reference table with the current calculated value for $\Delta T_m$. If the threshold value exceeds the calculated value, the audible alarm may be activated in order to alert medical personnel of a problem. In addition, the difference between the threshold value and the calculated value may be used by the microprocessor to determine which combination of the LEDs should be illuminated.

In another embodiment of the invention, the reference table may be thought of as having three dimensions. Along a first axis of the reference table may be a set of possible values of $T_a$, along the second axis of the reference table may be a set of possible values of $T_{bias}$, and along the third axis of the reference table may be a set of possible $\Delta T_m$ values. The values for $T_a$, $T_{bias}$ and $\Delta T_m$ may be re-calculated frequently, for example each second. Together, the values for $T_a$, $T_{bias}$, and $\Delta T_m$ identify a "location" in the reference table, which may include a pointer that identifies the location of a set of instructions that the microprocessor should carry out. For example, the current values of $T_a$, $T_{bias}$, and $\Delta T_m$ may point (via the reference table) to instructions, which when executed by the microprocessor result in three of the light emitting diodes from the LED array being illuminated and the audio device being turned off. By using $T_a$, $T_{bias}$, and $\Delta T_m$ in this fashion, changes such as a change in the gas flow (oxygen and/or air) can be accommodated without significantly altering the breathing indication provided by the device to medical personnel.

The invention can be used to create a device, which is low cost, portable, continuous and reliable. Further, the invention can be implemented as a lightweight device. Also, a small handheld device according to the invention can operate using an internal battery, as well as an approved wall power adapter. This feature allows for temporary transport and operation, as well as extended operation of the unit when necessary.

In addition, a memory device can be included which will extract and store information about the patient's breathing. Later, the information in the memory can be accessed, downloaded and analyzed.

In addition, this device can be equipped to transmit the acquired thermistor data to a data processing computer that provides additional enhanced capabilities to medical personnel. The data processing computer can store the data for later analysis, provide long term trend graphs of the raw and processed data, and assist in both long term studies as well as real time monitoring using powerful visual displays such as graphs, charts and LED's.

It will now be recognized that a device according to the invention can be a powerful tool for detecting apnea and hypoxia.

Figure 2:
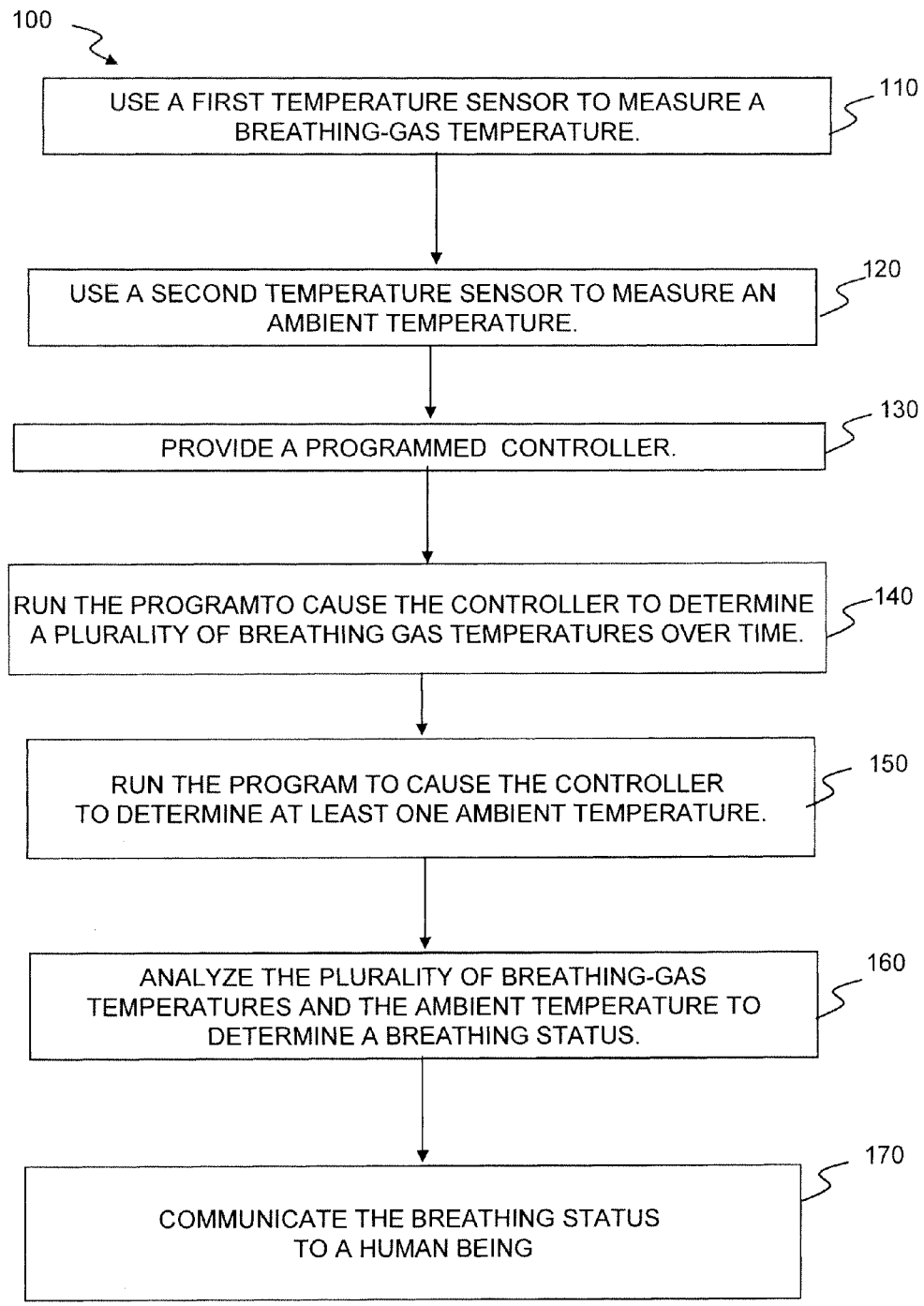
FIG. 2 is a flowchart showing a method according to an embodiment of the present invention.

FIG. 2 depicts a method that is in keeping with the invention. Such a method 100 may be for monitoring the breathing of a patient in accordance with the system described above. A first temperature sensor may be provided and used 110 to measure the patient's breathing-gas temperature, $T_m$, and a second temperature sensor may be provided and used 120 to measure an ambient temperature, $T_a$. A controller may be provided 130, the controller being programmed to determine a plurality of breathing-gas temperatures over time, $T_m(t)$, using a first signal received from the first temperature sensor. Also, the controller may be programmed to determine at least one ambient temperature, $T_a(t)$, using a second signal received from the second temperature sensor. The controller may be further programmed to analyze the plurality of breathing-gas temperatures and the at least one ambient temperature to determine a breathing status of the patient.

By running the program, the controller may be used to determine 140 a plurality of breathing gas temperatures over time, and to determine 150 at least one ambient temperature. The controller may be used to analyze the breathing gas temperatures and ambient temperature(s), and to determine 160 a breathing status of the patient. The breathing status of the patient may be communicated 170 to a human being, such as a nurse or doctor. Furthermore, if the breathing status is determined 160 to be unsatisfactory, the communication 170 may include activation of a visual and/or audio alarm.

The program used to instruct the controller to determine a plurality of breathing-gas temperatures may determine a maximum breathing-gas temperature, $Max(T_m(t))$, and a minimum breathing-gas temperature, $Min(T_m(t))$, during a time interval, which may be a breathing period, such as a respiratory cycle. The program used to instruct the controller to analyze the temperatures may instruct the controller to calculate a mathematical difference, $\Delta T_m = Max(T_m(t)) - Min(T_m(t))$, and compare the calculated $\Delta T_m$ to a threshold $\Delta T_m$. The controller may indicate the breathing status of the patient. For example, if the calculated $\Delta T_m$ is less than the threshold $\Delta T_m$, the breathing status of the patient may be indicated to be unsatisfactory. The controller may activate an alarm if the breathing status of the patient is unsatisfactory.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A breathing monitoring system, comprising:
   a) a first temperature sensor arranged to measure a patient's breathing-gas temperature;

b) a second temperature sensor arranged to measure an ambient temperature; and
c) a controller programmed to:
  i) determine a plurality of breathing-gas temperatures over a time interval using a first set of signals received from the first temperature sensor;
  ii) determine at least one ambient temperature during said time interval using a second signal received from the second temperature sensor;
  iii) compute a maximum breathing-gas temperature and a minimum breathing-gas temperature from said first set of signals;
  iv) calculate a difference between said maximum and minimum breathing-gas temperatures ("$\Delta Tm$");
  v) compute a temperature threshold difference ("threshold $\Delta Tm$") as a function of the ambient temperature; and
  vi) compare the threshold $\Delta Tm$ to said $\Delta Tm$ to determine a breathing status of said patient.

2. The system of claim 1, wherein the controller is programmed to analyze the plurality of breathing-gas temperatures by determining said maximum breathing-gas temperature and said minimum breathing-gas temperature during said time interval, the time interval corresponding to a period of the patient's inhalation/exhalation cycle.

3. The system of claim 2, wherein the controller is programmed to analyze the plurality of breathing-gas temperatures by comparing the calculated $\Delta Tm$ with said threshold $\Delta Tm$, wherein if the calculated $\Delta Tm$ is less than the threshold $\Delta Tm$, the breathing status of the patient is unsatisfactory.

4. The system of claim 3, further comprising an alarm in communication with the controller, wherein the controller is programmed to activate the alarm if the breathing status of the patient is unsatisfactory.

5. The system of claim 3, wherein the controller is programmed to:
  (a) calculate a bias temperature ("Tbias"), Tbias being the mathematical difference of an average breathing-gas temperature and a time-based average ambient temperature; and
  (b) determine the threshold $\Delta Tm$ from the ambient temperature and Tbias.

6. The system of claim 5, wherein the controller comprises a memory device having a pre-defined look-up table, and wherein the controller is programmed to determine the threshold $\Delta Tm$ from the ambient temperature and Tbias by using the ambient temperature and Tbias to look up a threshold $\Delta Tm$ in the look-up table.

7. The system of claim 5, wherein the controller comprises a field-programmable gate array ("FPGA"), and the FPGA is programmed to determine the threshold $\Delta Tm$ from the ambient temperature and Tbias.

8. The system of claim 7, wherein the FPGA is programmed to use a decision-tree to determine the threshold $\Delta Tm$ based on the values of the ambient temperature and Tbias.

9. The system of claim 5, wherein the controller comprises a memory device having a pre-defined multi-dimensional look-up table, the look-up table relating a plurality of pre-defined program steps to particular combinations of ambient temperature, $\Delta Tm$, Tbias values, and the controller is programmed to determine a program step based on the measured ambient temperature and calculated $\Delta Tm$ and Tbias.

10. The system of claim 9, wherein the controller is programmed to execute the determined program step.

11. The system of claim 5, wherein the controller is programmed to use a decision-tree to determine the threshold $\Delta Tm$ based on the values of the ambient temperature and Tbias.

12. A method for monitoring the breathing of a patient, comprising the steps of:
  a) using a first temperature sensor to measure the patient's breathing-gas temperature during a time interval;
  b) using a second temperature sensor to measure an ambient temperature; and
  c) providing a controller programmed for:
    i) determining a plurality of breathing-gas temperatures over said time interval using a first set of signals received from the first temperature sensor;
    ii) determining at least one ambient temperature using a second signal received from the second temperature sensor; and
    iii) computing a maximum breathing-gas temperature and a minimum breathing-gas temperature from said first set of signals;
    iv) calculating a difference between said maximum and minimum breathing-gas temperatures ("$\Delta Tm$");
    v) computing a temperature threshold difference ("threshold $\Delta Tm$") as a function of the ambient temperature; and
    vi) comparing the threshold $\Delta Tm$ to said $\Delta Tm$ to determine a breathing status of the patient.

13. The method of claim 12, wherein communicating the breathing status of the patient comprises using the controller to activate an alarm if the breathing status of the patient is determined to be unsatisfactory.

14. The method of claim 12, wherein the controller is programmed to analyze the plurality of breathing-gas temperatures by determining said maximum breathing-gas temperature and a minimum breathing-gas temperature during said time interval, the time interval corresponding to a period of the patient's inhalation/exhalation cycle.

15. The method of claim 14, wherein the controller is programmed to analyze the plurality of breathing-gas temperatures by comparing the calculated $\Delta Tm$ with said threshold $\Delta Tm$, wherein if the calculated $\Delta Tm$ is less than the threshold $\Delta Tm$, the breathing status of the patient is unsatisfactory.

* * * * *